United States Patent [19]

Miller et al.

[11] 4,257,773

[45] Mar. 24, 1981

[54] ASSAY METHOD AND COMPOUNDS

[75] Inventors: Richard J. Miller, Raleigh; Kwen-Jen Chang; Pedro Cuatrecasas, both of Chapel Hill, all of N.C.

[73] Assignee: Burroughs Wellcome Co., Research Triangle Park, N.C.

[21] Appl. No.: 52,967

[22] Filed: Jun. 28, 1979

Related U.S. Application Data

[62] Division of Ser. No. 841,678, Oct. 13, 1977.

[51] Int. Cl.$^3$ .................. C07C 103/52; A61K 43/00; G01N 33/68
[52] U.S. Cl. ................. 23/230 B; 23/230.3; 260/112.5 R; 422/61; 424/1; 424/1.5; 435/7; 435/29
[58] Field of Search .................. 424/1, 1.5; 23/230.3, 23/230 B; 260/112.5 R; 422/61; 435/7, 29

[56] References Cited

PUBLICATIONS

Pert et al., Opiates and Endogenous Opioid Peptides 1976 pp. 79-86.
A. Wahlstrom et al., Opiates and Endogenous Opioid Peptides (1976) pp. 41-48.
Beddell, CR, et al., Biological Abstracts, Sep. 1978 29363.
R. J. Miller et al., Biochem. and Biophys. Res. Communication, 74, 1977 pp. 1311-1317.
Li et al., Biochem. Biophys. Res. Commun. 1977 75/3 576-580.
Guillemin, et al., Biochem. Biophys. Res. Commun., 1977 77/1 361-366.
Chang et al., Int. J. Pept. Protein Res. 1978 11/1, 93-94.
Miller et al., J. Biol. Chem. 1978, 253/2, 531-538.
Miller et al., Life Sci. 1978, 22/5 379-387.
Austin, et al., Nature, 269 No. 5629, 619-1977.

*Primary Examiner*—Michael S. Marcus
*Attorney, Agent, or Firm*—Donald Brown

[57] ABSTRACT

The present invention provides an assay method for opioid activity comprising the steps of:
  (a) incubating together an opiate receptor material, a radio-iodinated structural analogue of leucine-enkephalin or methionine-enkephalin, and a liquid sample;
  (b) measuring the percentage inhibition of the binding of the radio-iodinated compound to the opiate receptor material; and
  (c) determining the opioid activity of the liquid sample using the percentage inhibition measurement.

Also provided are a test kit of value in the performance of such assays, and novel compounds of use in such assays together with methods for their preparation.

15 Claims, 2 Drawing Figures

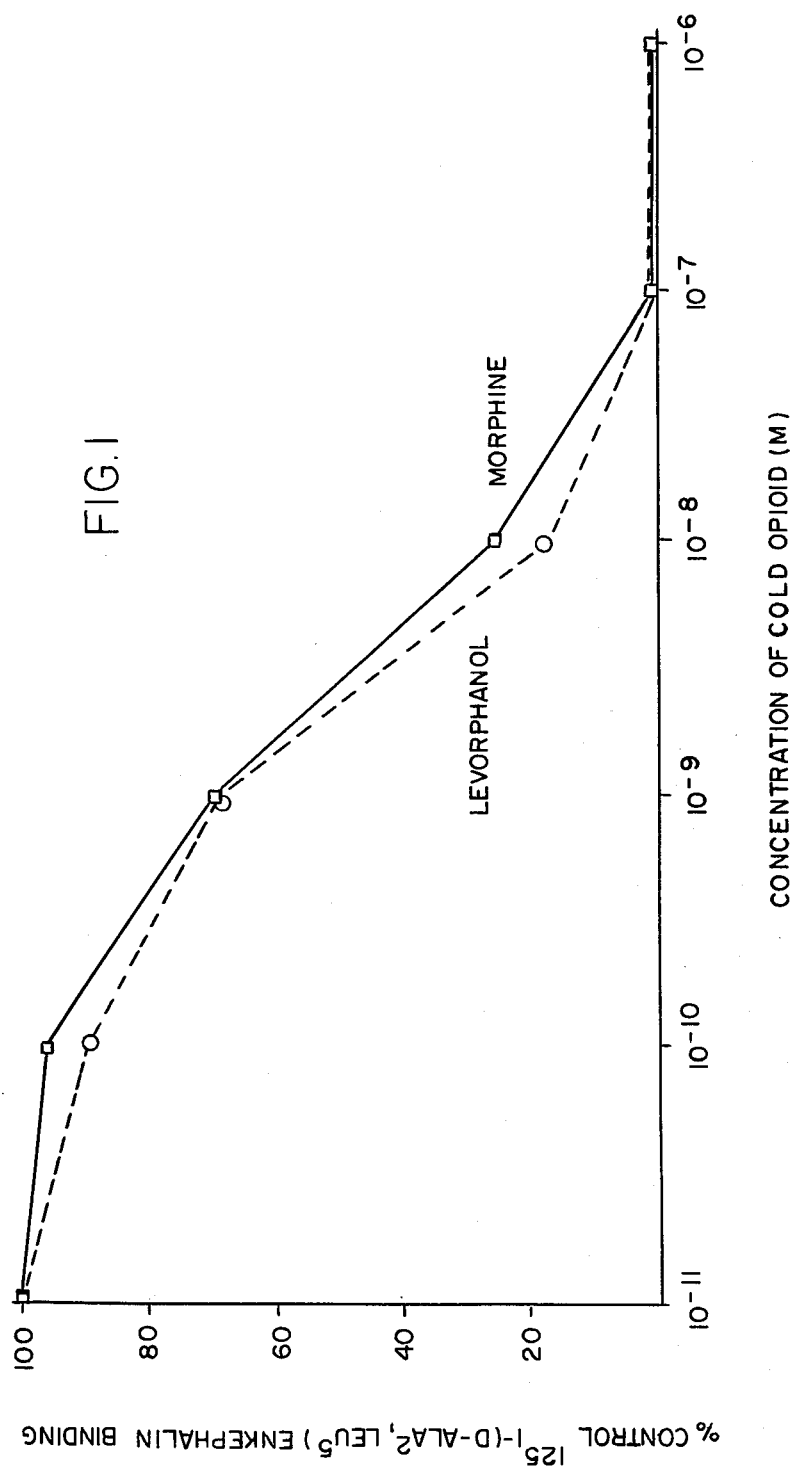

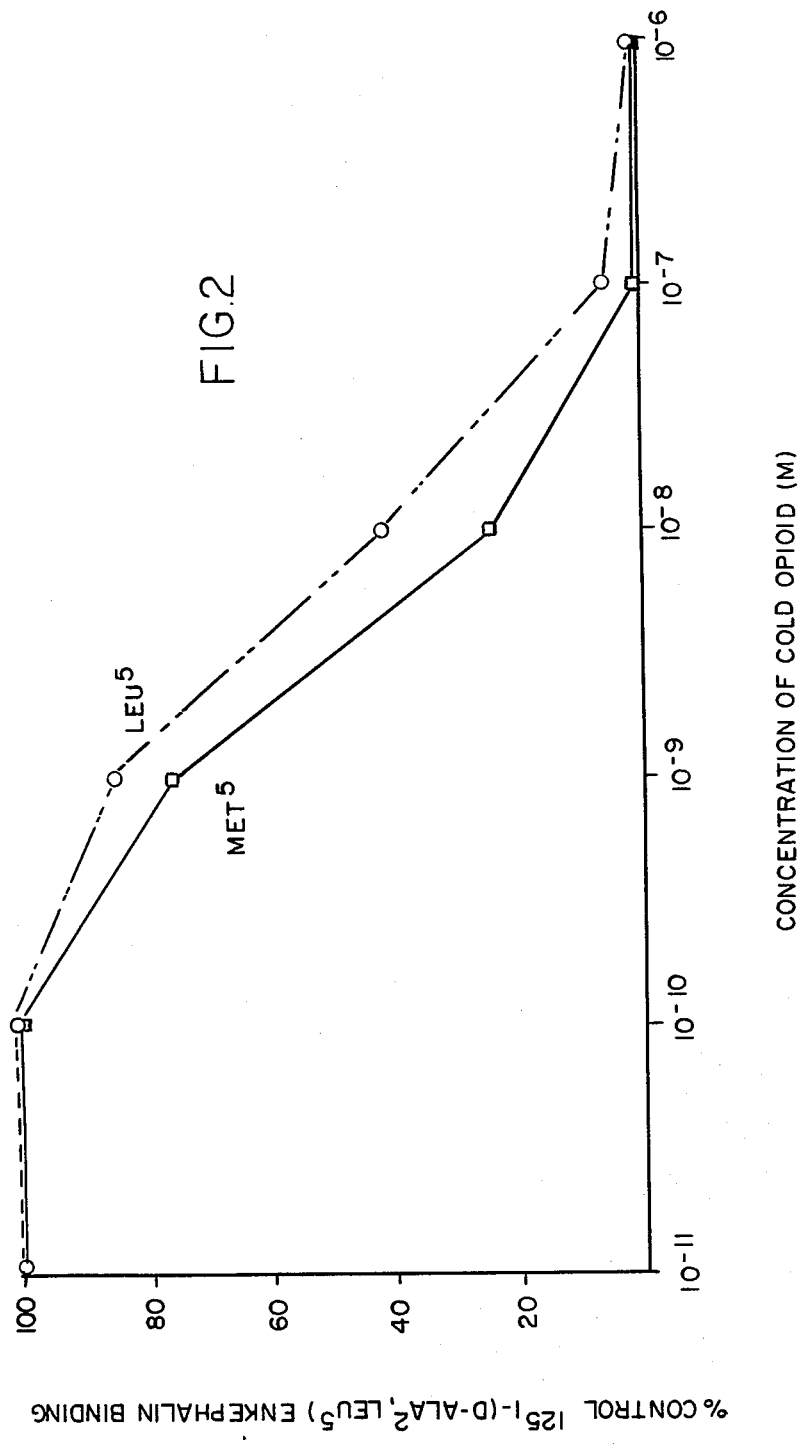

ASSAY METHOD AND COMPOUNDS

This is a division, of application Ser. No. 841,678 filed Oct. 13, 1977.

This invention relates to a method for the assay of opioid activity in liquids, to a test kit of value in the performance of such assays, and to novel compounds of use in such assays and the preparation of such compounds.

As generally accepted and as used herein, the term opioid refers to any natural or synthetic drug that has morphine-like pharmacological actions.

Opioid drugs such as morphine, diacetylmorphine (heroin), levorphanol, pentazocine and phenazocine have found clinical acceptance in varying degrees and their respective pharmacological properties and therapeutic indications are well documented in the literature, see for example "The Pharmacological Basis of Therapeutics", Goodman, L. S. and Gilman, A. eds., published by the Macmillan Publishing Co., Inc., New York, fifth edition (1975) especially at Chapter 15, pages 245 to 283, and "Martindale: The Extra Pharmacopoeia", Blacow, N. W. ed., published by The Pharmaceutical Press, London, twenty-sixth edition (1972) especially at pages 1100 to 1139, all of which is incorporated herein by reference hereto. As is well known however (Goodman, L. S. et. al., loc. cit., chapter 16) repeated administration of members of this class of drug, sometimes termed the narcotic analgesics, and especially of morphine and diacetylmorphine (heroin), can lead to the recipient developing an addiction to the drug and tolerance to its effects and to his manifesting withdrawal symptoms when administration is discontinued. The problems, both medical and social, arising from opioid drug abuse have long been felt and in recent times several agencies, notably the armed forces and law enforcement agencies, as well as hospitals and the medical profession in general have recognised the need for an assay method for opioids in human body fluids.

At present no really convenient assay method is available. The most commonly used procedure involves extraction of the drug from the body fluid followed by gas or liquid chromatographic techniques. Although this method is accurate it is also quite costly and very time-consuming, and requires a great deal of technical knowledge and sophisticated equipment. Moreover these techniques are applicable only for individual drugs rather than for the whole class of opioids. In the particular case of morphine a radioimmunoassay technique is available but although this method is convenient in some respects the specificity of the antisera used makes it unsuitable for assaying other opioids.

The fairly stringent chemical requirements for opioid activity, the fact that opioid effects are highly stereospecific and the extreme potency of some opioids have long suggested that opioid actions involve highly selective sites or receptors in the brain, and the regional distribution of these opiate receptors in monkey, human, bovine and rat brain has been investigated (Kuhar, M. J. et. al., Nature, 245, 447-450 (1973) and Snyder, S. H., Nature, 257, 185-189 (1975)). In recent years receptor binding assays have been developed as tools for the investigation of the loci of action of drugs and hormones and assays of this type, specific for opioids, have been used to examine the properties of the opiate receptor, see for example Pert, C. B. et. al., *Molecular Pharmacology*, 10, 868-879 (1974). Such assays depend upon the natural specificity of the drug (or hormone) for its natural receptor site: the receptors have very high affinity for the compound and if low concentrations of radioactively labelled drug are incubated with tissue preparations containing such receptors the majority of the drug will bind selectively to the receptors and will be displaceable therefrom by non-radioactive ("cold") drug(s) having the same loci of action. The opioid receptor binding assays have to date relied on the binding to opiate receptors of tritiated opioid agonists (such as etorphine) or tritiated opioid antagonists (such as naloxone), with the associated disadvantages of low specific radioactivity and the need for measuring samples in a liquid scintillation counter (Pert et. al., loc. cit.)

According to one aspect of the present invention there is now provided an assay method for opioid activity comprising the steps of (a) incubating together an opiate receptor material, a radio-iodinated opioid (as hereafter defined), and a liquid sample;

(b) measuring the percentage inhibition of the binding of the radio-iodinated compound to the opiate receptor material; and (c) determining the opioid activity of the liquid sample using the percentage inhibition measurement.

This method may be used for the assay of opioid activity of aqueous solutions and of body fluids, for example body fluids of human or other mammalian origin such as blood plasma, blood serum, urine, saliva and cereb rospinal fluid. The method enables the assay of total opioid activity, being specific for opioids as a class but lacking specificity within that class, and has the important advantages when compared with methods previously available of wide applicability, cheapness and ease and speed of performance; the radioiodine label enables the preparation and use of opioids of high specific radioactivity and permits measurements to be made with the solid crystal type of scintillation counter.

The method of the present invention may be used for the assay of total opioid activity of samples containing one or more of the following opioids in clinical use, although this list is by way of exemplification only and is neither exhaustive nor limiting: morphine, acetorphine, benzylmorphine, codeine, diacetylmorphine (heroin), dihydrocodeine, ethylmorphine, etorphine, dihydrocodeinone, hydromorphinol, dihydromorphinone, levorphanol, oxycodone, oxymorphone, pentazocine, phenazocine, acethydrocodone, alphaprodine, anileridine, dextromoramide, dextropropoxyphene, diphenoxylate, dipipanone, ethoheptazine, phentanyl, ketobemidone, methadone, metofoline, pethidine, phenadoxone, phencyclidine, phenoperidine, piminodine, racemoramide and trimeperidine.

The present method is applicable also to the assay of samples containing either or both of the pentapeptides leucine-enkephalin (H-L-tyrosyl-glycyl-glycyl-L-phenylalanyl-L-leucyl-OH) and methionine-enkephalin (H-L-tyrosyl-glycyl-glycyl-L-phenylalanyl-L-methionyl-OH) isolated from brain and characterised by Hughes et. al. (*Nature*, 258, 577-579 (1975)) and/or one or more of the other endogenous opioid factors described in the literature, for example α-endorphin (Lazarus, L. H. et. al., (1976) *Proc. Nat. Acad. Sci.,* 73, 2156-2159) and the C-fragment (residues 61-91) of β-lipotropin (Bradbury, A. F. et. al. (1976) *Nature*, 260, 793-795), and it will be appreciated that such endogenous materials will, if present, contribute to the total opioid activity as assayed by this method of for example a sample of human body fluid.

The source of the opiate receptor material can be any animal tissue having a high concentration of opiate receptors and can be derived from avian or mammalian species, for example ox, pig, sheep, rodent or man. Mammalian brain tissue is preferred and from a practical standpoint one of the most convenient sources of opiate receptor material is calf or ox brain which is readily obtainable from slaughterhouses. It is known that there are considerable regional differences in the concentration of opiate receptors in the mammalian brain (Snyder, S. H. and Kuhar et. al., loc. cit.) and, if desired, the brain(s) providing the receptor material may be initially dissected to isolate those areas having particularly high concentrations of receptors.

For use in the assay the material providing the opiate receptors, for example calf brain, is initially homogenized using any of the appropriate art techniques such as that of Pasternak, G. W. et. al., *Molecular Pharmacology*, 11, 340-351 (1975). The opiate receptors in mammalian brain tissue are localized in synaptic membranes and, if desired, the initially prepared crude brain homogenate may be fractionated to provide a fraction wherein the opiate receptors are concentrated, for example by the method of Pert, C. B. et. al., *Brain Research*, 70, 184-188 (1974).

In one embodiment the assay is performed using aqueous, preferably buffered, suspensions of the crude homogenate or receptor-enriched fraction thereof. Until required for use such materials may be held in sealed vessels, either in suspension in an aqueous liquid medium or in a lyophilized state, in the latter case being reconstituted immediately prior to use by the addition of, for example, an aqueous buffer solution. In an alternative embodiment the opiate receptor material (crude homogenate or receptor-enriched fraction) is for the duration of the assay adhered to a solid support, for example glass beads or the wall of a suitable container such as a tube compatible with a solid crystal scintillation counter. In this embodiment the receptor material, adhered to the support, is conveniently held in a lyophilised state and reconstituted prior to use with an aqueous buffer solution.

As another source of opiate receptor material may be mentioned those cell lines possessing opiate receptors, for example the neuroblastoma X glioma hybrid NG108-15 of Sharma, S. K. et. al., *Proc. Nat. Acad. Sci.*, 72/2, 590-594 (1975). Such cells may be used in the assay either intact or after disintegration: in the latter case the resulting crude homogenate may itself be used in the assay or may be fractionated to provide a receptor-enriched fraction. These materials may be used in the assay as suspensions or when adhered to a solid support in an analogous manner to that described above in respect of receptor material derived from brain tissue and may be stored and, as appropriate, reconstituted in a similar fashion.

In a second aspect the present invention provides novel radio-iodinated peptide opioids, suitable for use in the assay method hereinbefore described, which are structural analogues of the natural leucine- and methionine-enkephalins (Hughes et. al., loc. cit.) and whereof the corresponding non-iodinated compounds have an affinity ($IC_{50}$) for the opiate receptor, measured by the method of Pasternak et. al., loc. cit. using tritiated naloxone and in the absence of sodium ions, of at least $10^{-8}$ M.

The radio-iodinated compounds may be prepared from the corresponding non-iodinated compounds using any of the appropriate radio-iodination techniques available in the art and conveniently (for those compounds which include a tyrosyl residue) by the method of Hunter, W. M. et. al., *Nature*, 194, 495-496 (1962) using "chloramine T" ((N-chloro-p-toluenesulphonamido)sodium). It will be appreciated that in principle any of the radioisotopes of iodine ($^{123}$I, $^{124}$I, $^{125}$I, $^{126}$I, $^{128}$I, $^{129}$I, $^{130}$I, $^{131}$I and $^{132}$I) may be used to prepare the radio-iodinated compounds but that, from considerations of availability, half-life and specific activity, $^{125}$I and $^{131}$I are preferred and $^{125}$I most preferred.

It is believed that in the radio-iodination of compounds containing a tyrosyl residue the iodine label is introduced into the tyrosyl phenol moiety at either the 2-position or at both the 2- and 6-positions with respect to the hydroxy group; of these the mono-iodo compounds are preferred for the assay of the present invention.

A preferred class of radio-iodinated compounds are those whereof the corresponding non-iodinated compounds have an affinity for the opiate receptor, as above defined, of at least $10^{-9}$ M.

As a class of radio-iodinated compounds of the present invention are the peptides of formula (I):

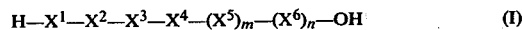

wherein $X^1$ is selected from L-tyrosyl and N-alkyl-L-tyrosyl (wherein the alkyl has 1 to 4 carbon atoms) substituted in the phenol moiety at the 2-position or at both the 2- and 6-positions (with respect to the hydroxy group) with an iodine radioisotope;

$X^2$ is selected from glycyl and D-alanyl;

$X^3$ is selected from glycyl and L-alanyl;

$X^4$ is selected from L-phenylalanyl and L-4-chlorophenylalanyl;

$X^5$ is selected from L-leucyl, D-leucyl, L-methionyl, D-methionyl, L-valyl, D-valyl, L-norleucyl, D-norleucyl, L-threonyl and D-threonyl;

$X^6$ is L-threonyl;

and m and n are each selected from 0 and 1, provided that when they are both 0 then $X^2$ is D-alanyl;

together with their salts, esters, amides and N-alkylamides wherein the alkyl has 1 to 4 carbon atoms.

As a subclass within formula (I) may be mentioned those peptides of the formula:

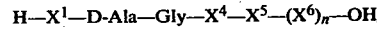

wherein $X^1$ is L-tyrosyl substituted in the phenol moiety at the 2-position or at both the 2- and 6-positions (with respect to the hydroxy group) with an iodine radioisotope;

D-Ala is D-alanyl;

Gly is glycyl;

$X^4$ is selected from L-phenylalanyl and L-4-chlorophenylalanyl;

$X^5$ is selected from L-leucyl, D-leucyl, L-methionyl, D-methionyl, L-norleucyl and D-norleucyl;

$X^6$ is L-threonyl;

and n is selected from 0 and 1; together with their salts and esters.

Within formula (I):

$X^1$ is preferably L-tyrosyl or N-alkyl-L-tyrosyl substituted in the phenol moiety at the 2-position (with respect to the hydroxy group) with an iodine radioisotope, and when $X^1$ is N-alkyl-L-tyrosyl the alkyl is preferably methyl or ethyl;

the esters are preferably alkyl esters, for example wherein the alkyl has 1 to 4 carbon atoms such as the methyl and ethyl esters, or are aryl esters, for example wherein the aryl is phenyl or halophenyl where the halo is for example chloro as in p-chlorophenyl; and the N-alkylamides are preferably selected from the N-methylamide and the N-ethylamide.

The non-iodinated compounds from which the radio-iodinated compounds are prepared may themselves be prepared by any of the methods known in the art for the synthesis of compounds of analogous structure. Thus they may be prepared by for example the conventional solution method, dicyclohexylcarbodiimide-mediated coupling, or by the repetitive mixed anhydride method described by Tilak (*Tetrahedron Lett*, 849–854 (1970)) and by Beyerman (*Helv. Chim. Acta.*, 56, 1729–1740 (1973)).

In the performance of the assay method of the present invention a radio-iodinated opioid (as above described) and an aliquot of the liquid to be assayed are incubated for an appropriate period of time and at an appropriate temperature with an opiate receptor material. At the end of the incubation period the (insoluble) opiate receptor material is isolated from the mixture and the radioactivity bound to the material is measured. The percentage inhibition of the binding of the radio-iodinated compound to the opiate receptor material is determined by comparison with the results obtained with control incubations. The opioid activity of the test liquid is then determined by reference to a standard curve quantified in a convenient manner, for example with reference to an opioid such as morphine. If the test liquid is known to contain but a single, identified opioid a standard curve of the same compound could be used.

Desirably the incubation is effected in a buffer solution providing a pH in the range 6 to 9 and preferably in the range 7 to 8, for example TRIS (tris(hydroxymethyl)aminomethane) hydrochloric acid buffer of pH 7.4 to 7.7. Other suitable buffers include sodium phosphate buffer and glycine buffer. The incubation mixture can include any of numerous additives to facilitate binding or to protect the mixture components. Although the duration of the incubation and the temperature at which it is effected can be varied and involve any convenient period it is generally preferable to conduct the incubation to equilibrium, suitable times being in the range 2 minutes to 4 hours. The opiate receptor material may be isolated from the mixture by any suitable technique including filtration and centrifugation; where filtration is used the filter material should of course be such that the opiate receptor material is thereby retained.

A test-kit suitable for use in the assay method of the present invention comprises at least (a) a first sealed vessel containing an opiate receptor material; and (b) a second sealed vessel containing a radio-iodinated opioid (as above described), the contents of each of the vessels optionally being in a lyophilised state.

The following Examples are provided by way of illustration of the present invention and should not be construed as in any way constituting a limitation thereof. All temperatures are in degrees Celsius. The abbreviations used herein for amino acids and their radicals are those conventional in the art and may be found in, for example, *Biochemistry*, 11, 1726 (1972). All references herein are to the L-amino acids and their radicals except in the case of glycine and unless otherwise stated. C-Terminal derivatives are indicated according to convention, that is to say:

—OMe: methyl ester
—NH$_2$: amide
—NHEt: ethylamide

Each of the references recited herein is incorporated herein by reference thereto. Wherever herein reference is made to salts of the radio-iodinated compounds these should be understood as those salts that are pharmacologically compatible with the other components of the incubation mixture as herein described.

It will be appreciated from the foregoing that what we will claim may comprise any novel feature described herein, principally and not exclusively, for example:

(a) an assay method for opioid activity comprising the steps of (i) incubating together an opiate receptor material, a radio-iodinated opioid (as herein defined), and a liquid sample;

(ii) measuring the percentage inhibition of the binding of the radio-iodinated compound to the opiate receptor material; and (iii) determining the opioid activity of the liquid sample using the percentage inhibition measurement;

(b) radio-iodinated structural analogues of leucine-enkephalin and methionine-enkephalin whereof the corresponding non-iodinated compounds have an affinity (IC$_{50}$) for the opiate receptor, measured by the method of Pasternak et. al., loc. cit. using tritiated naloxone and in the absence of sodium ions, of at least $10^{-8}$ M;

(c) a method for the preparation of the compounds defined in para. (b) comprising radio-iodination of the corresponding non-iodinated compounds;

(d) a test kit comprising at least (i) a first sealed vessel containing an opiate receptor material, and (ii) a second sealed vessel containing a compound defined in para. (b), the contents of each of the vessels optionally being in a lyophilised state;

(e) peptides of formula (I) as hereinbefore defined wherein $X^2$ is D-alanyl.

EXAMPLE 1

Preparation of radio-iodinated opioids

The following peptides were prepared by methods standard in peptide chemistry and found to have the characterising data respectively shown therefor.

(A) H.Tyr.D-Ala.Gly.Phe.Leu.OH HCl
(B) H.Tyr.D-Ala.Gly.Phe.Met.OH HCl
(C) H.Tyr.D-Ala.Gly.Phe.D-Leu.OH HCl

|     | $[\alpha]_D^{25}$(in methanol) | Opiate receptor IC$_{50}$(M)* |
|-----|-------------------------------|-------------------------------|
| (A) | +19.8° (c = 0.5)              | 3.2 × 10$^{-9}$              |
| (B) | +17.2° (c = 0.5)              | 3.8 × 10$^{-9}$              |
| (C) | +31.5° (c = 0.53)             | 2.6 × 10$^{-9}$              |

*Method of Pasternak, G. W. et al., Molecular Pharmacology, 11, 340–351 (1975) using tritiated naloxone and in the absence of sodium ions; assays performed at 4° C. in the presence of bacitracin (50 µg/ml) in tris-hydrochloric acid buffer (50 mM, pH 7.4).

Compound (A) was radio-iodinated according to the following procedure.

To sodium phosphate buffer (0.25 M, pH 7.4, 0.1 ml) were added compound (A) (1.5 μg) and carrier-free iodine—125 (Union Carbide) (3mCi). Chloramine T ((N-chloro-p-toluenesulphonamido)sodium) (20 μl. of a 0.5 mg/ml aqueous solution) was added to the mixture followed after 20 sec. by sodium metabisulphite (20 μl. of a 1 mg/ml. aqueous solution). The mixture was then chromatographed on a Biogel P2 column (100–200 mesh) using sodium phosphate buffer (0.25 M, pH 7.4) containing 0.1% bovine serum albumin as eluant. The void volume peak was very small (sometimes absent) and was followed by a large major peak of radioactivity containing the radio-iodinated opioid.

The material comprising this peak was applied to a Sephadex 2-(diethylamino)ethyl ether column and eluted with sodium borate buffer (12.5 mM, pH 9.0, 0.1 N sodium chloride). Two peaks of radio-activity resulted, the material of the first peak having a greater specific binding affinity (for the opiate receptor) than that of the second peak.

The material of the first peak was identified as the monoiodinated compound,

H.Tyr(3-$^{125}$I).D-Ala.Gly.Phe.Leu.OH while the material of the second peak was identified as the corresponding diiodinated compound, H.Tyr(3,5-$^{125}$I).D-Ala.Gly.Phe.Leu.OH By analogous procedures to those detailed above there were prepared the monoiodinated and diiodinated derivatives of compounds (B) and (C), that is to say H.Tyr(3-$^{125}$I).D-Ala.Gly.Phe.Met.OH
H.Tyr(3,5-$^{125}$I).D-Ala.Gly.Phe.Met.OH
H.Tyr(3-$^{125}$I).D-Ala.Gly.Phe.D-Leu.OH
H.Tyr(3,5-$^{125}$I).D-Ala.Gly.Phe.D-Leu.OH

EXAMPLE 2

Preparation of radio-iodinated opioids

The peptides shown in Table 1 were prepared by methods standard in peptide chemistry and found to have the characterising data respectively shown therefor. The opiate receptor IC$_{50}$(M) was ascertained by the method indicated in Example 1.

Each of the peptides was radio-iodinated by an analogous procedure to that described in Example 1 to yield the corresponding Tyr(3-$^{125}$I) and Tyr(3,5-$^{125}$I) compounds.

EXAMPLE 3

Preparation of radio-iodinated opioids

The peptides shown in Table 2 were prepared by methods standard in peptide chemistry and found to have the characterising data respectively shown therefor. The opiate receptor IC$_{50}$(M) was ascertained by the method indicated in Example 1.

Each of the peptides was radio-iodinated by an analogous procedure to that described in Example 1 to yield the corresponding Tyr(3-$^{125}$I) and Tyr(3,5-$^{125}$I) compounds.

TABLE 1

| | Compound | $[\alpha]_D^{25}$(in methanol) | Opiate receptor IC$_{50}$(M) |
|---|---|---|---|
| (D) | H . Tyr . D-Ala . Gly . Phe . Met . OMe | +10.4° (c = 0.5) | 5 × 10$^{-9}$ |
| (E) | H . Tyr . D-Ala . Gly . Phe . Met . Thr . OH HCl | +12.46° (c = 0.52) | 5.6 × 10$^{-9}$ |
| (F) | H . Tyr . D-Ala . Gly . Phe . D-Leu . OMe HCl | +39.6° (c = 0.51) | 9 × 10$^{-9}$ |
| (G) | H . Tyr . D-Ala . Gly . Phe . Leu . Thr . OH HCl | +5.13° (c = 0.5) | 8 × 10$^{-9}$ |
| (H) | H . Tyr . D-Ala . Gly . Phe . Nle . OH HCl | +23.2° (c = 1.0) | 9 × 10$^{-9}$ |
| (J) | H. Tyr . D-Ala . Gly . Phe . D-Met . OH HCl | +31.0° (c = 0.51) | 8 × 10$^{-9}$ |
| (K) | H . Tyr . D-Ala . Gly . Phe(4Cl) . D-Leu . OH HCl | −4.56° (c = 0.2) | 1 × 10$^{-9}$ |
| (L) | H . Tyr . D-Ala . Gly . Phe(4Cl) .D-Leu . OMe HCl | +36.5° (c = 0.5) | 2 × 10$^{-9}$ |

EXAMPLE 4

Assay of opioid activity

Whole rat brains were homogenised in TRIS hydrochloric acid buffer (4° C., 50 mM, pH 7.4) and the mixture centrifuged (30 mins., 4° C., 50000×g). The resulting pellet was isolated and resuspended in a further quantity of the same buffer.

Aliquots (2 ml) of the brain homogenate suspension were incubated (25° C., 45 mins.) with (a) an aliquot (20 μl) of an aqueous standard solution of morphine, and (b) the compound H.Tyr(3-$^{125}$I).D-Ala.Gly.Phe.Leu.OH (Example 1) (2×10$^5$ c.p.m.)

At the end of the incubation period the mixture was filtered under vacuum through Whatman GFB glass fibre filters, the filters washed (2×5 ml) with ice-cold Tris-hydrochloric acid buffer as used to suspend the brain homogenate pellet, and the filters then counted in a solid crystal scintillation counter.

The incubation was repeated, using fresh materials in every instance, with aliquots of aqueous standard solutions of levorphanol.

TABLE 2

| | Compound | $[\alpha]_D^{25}$(in methanol) | Opiate receptor IC$_{50}$(M) |
|---|---|---|---|
| (M) | H . Tyr . Gly . Gly . Phe . Val . OH HCl | +31.7° (c = 0.1) | 8 × 10$^{-8}$ |
| (N) | H. Tyr . D-Ala . Ala . Phe . Leu . OH HCl | +1.68° (c = 0.5) | 8 × 10$^{-8}$ |
| (O) | H . Tyr . Gly . Gly . Phe . Nle . OH HCl | +24.44° (c = 0.4) | 8 × 10$^{-8}$ |
| (P) | H . Tyr . Gly . Gly . Phe . D-Leu . OH HCl | +28.7° (c = 0.4) | 2.5 × 10$^{-8}$ |
| (Q) | H. Tyr . D-Ala . Gly . Phe . Thr . OH HCl | +19.8° (c = 0.51) | 9 × 10$^{-8}$ |
| (R) | H . Tyr . D-Ala . Gly . Phe . D-Leu . Thr . OH HCl | +51.5° (c = 0.52) | 3 × 10$^{-8}$ |
| (S) | H . Tyr . D-Ala . Gly . Phe . D-Met . Thr . OH HCl | +47.8° (c = 0.51) | 7 × 10$^{-8}$ |
| (T) | H . Tyr . D-Ala . Gly . Phe . OH HCl | +64.6° (c = 0.5) | 7 × 10$^{-8}$ |
| (U) | H . Tyr . D-Ala . Gly . Phe . D-Leu . p-chlorophenyl ester HCl | +38.9° (c = 0.5) | 5 × 10$^{-8}$ |
| (V) | H . MeTyr . D-Ala . Gly . Phe . D-Leu . OH HCl | +40.9° (c = 1) | 3 × 10$^{-8}$ |
| (W) | H . Tyr . Gly . Gly . Phe . D-Leu . OMe HCl | +40.0° (c = 0.5) | 6 × 10$^{-8}$ |
| (X) | H . MeTyr . D-Ala . Gly . Phe . D-Leu . NH$_2$ HCl | +50.7° (c = 1) | 2 × 10$^{-8}$ |
| (Y) | H . Tyr . Gly . Phe . D-Met . OMe HCl | +43.7° (c = 0.5) | 6 × 10$^{-8}$ |
| (Z) | H . Tyr . Gly . Gly . Phe . D-Met. OH HCl | +38.3° (c = 0.5) | 1 × 10$^{-8}$ |

TABLE 2-continued

| Compound | $[\alpha]_D^{25}$(in methanol) | Opiate receptor $IC_{50}(M)$ |
|---|---|---|
| (A1) H . Tyr . D-Ala . Gly . Phe(4Cl) . D-Leu . NHEt HCl | +40.7° (c = 0.5) | $8 \times 10^{-8}$ |

The standard curves shown in FIG. 1 were obtained (all points are the mean of three separate determinations).

In FIG. 1, the compound identified as "$^{125}$I-(D-ALA$^2$, LEU$^5$)Enkephalin" is the radio-iodinated compound indicated hereinbefore.

EXAMPLE 5

Assay of opioid activity

Cells of the line identified as NG108-15 (Sharma, S. K. et al., *Proc. Nat. Acad. Sci.*, 72/2, 590–594 (1975)) were grown to confluence in monolayer, removed from the supporting medium and centrifuged at low speed, then washed twice with TRIS-hydrochloric acid buffer (150 mM, pH 7.4) and suspended in the same buffer at a final concentration of $10^6$ cells per ml.

Incubations (25° C., 45 mins.) were carried out in tubes each containing the following:

(a) Cell suspension as above (0.2 ml)
(b) Bacitracin (50 μg/ml)
(c) An aliquot (100 μl) of a standard solution in normal human serum of either methionine-enkephalin or leucine-enkephalin (Hughes, J. et al., *Nature*, 258, 577–579 (1975)); OR an aliquot (100 μl) of an unknown human serum; OR an aliquot (100 μl) of normal human serum; and
(d) the compound
H.Tyr(3-$^{125}$I).D-Ala.Gly.Phe.Leu.OH
(Example 1) (2 × 10$^5$ c.p.m.)

At the end of the incubation the cells were layered on top of a layer (100 μl) of oil (dinonyl phthalate:dibutyl phthalate, 2:1) in a microfuge tube and centrifuged (through the oil) for five minutes. The bottom of the tube, containing the cells as a pellet, was removed with a scalpel and counted in a solid crystal scintillation counter.

From the incubations conducted with methionine-enkephalin and leucine-enkephalin the standard curves shown in FIG. 2 where constructed (all points are the mean of three separate determinations). In FIG. 2, "MET$^5$" represents methionine-enkephalin, "LEU$^5$" represents leucine-enkephalin and the compound identified as "$^{125}$I-(D-ALA$^2$, LEU$^5$)Enkephalin" is the radio-iodinated compound indicated hereinbefore.

The total opioid activity of the mammalian body fluid, expressed in equivalents of leucine-enkephalin, was determined by reference to the standard curve obtained with the results of the leucine-enkephalin incubations.

What we claim is:

1. An assay method for opioid activity comprising the steps of
    (a) incubating together an opiate receptor material, a radio-iodinated compound of formula (I):

H—X$^1$—X$^2$—X$^3$—X$^4$—(X$^5$)$_m$—(X$^6$)$_n$—OH    (I)

wherein
    X$^1$ is selected from L-tyrosyl and N-alkyl-L-tyrosyl (wherein the alkyl has 1 to 4 carbon atoms) substituted in the phenol moiety at the 2-position or at both the 2- and 6-positions (with respect to the hydroxy group) with an iodine radioisotope;
    X$^2$ is selected from glycyl and D-alanyl;
    X$^3$ is selected from glycyl and L-alanyl;
    X$^4$ is selected from L-phenylalanyl and L-4-chlorophenylalanyl;
    X$^5$ is selected from L-leucyl, D-leucyl, L-methionyl, D-methionyl, L-valyl, D-valyl, L-norleucyl, D-norleucyl, L-threonyl and D-threonyl;
    X$^6$ is L-threonyl;
    and m and n are each selected from 0 and 1, provided that when they are both 0 then X$^2$ is D-alanyl; together with their salts, esters, amides and N-alkylamides wherein the alkyl has 1 to 4 carbon atoms, and a liquid sample;
    (b) measuring the percentage inhibition of the binding of the radio-iodinated compound to the opiate receptor material; and
    (c) determining the opioid activity of the liquid sample using the percentage inhibition measurement.

2. An assay method according to claim 1 wherein X$^2$ is D-alanyl.

3. An assay method according to claim 1 wherein the radio-iodinated compound is selected from
    H.Tyr(3-$^{125}$I).D-Ala.Gly.Phe.Leu.OH
    H.Tyr(3-$^{125}$I).D-Ala.Gly.Phe.Met.OH and
    H.Tyr(3-$^{125}$I).D-Ala.Gly.Phe.D-Leu.OH
    and salts thereof.

4. An assay method according to claim 1 wherein the liquid sample is of or is derived from a human body fluid.

5. An assay method according to claim 1 wherein the incubation step (a) is effected in a buffer solution providing a pH in the range 7 to 8.

6. The method of claim 1 in which the compound is H.Tyr(3-$^{125}$I).D-Ala.Gly.Phe.Leu.OH and salts thereof.

7. The method of claim 1 in which the compound is H.Tyr(3-$^{125}$I).D-Ala.Gly.Phe.Met.OH and salts thereof.

8. The method of claim 1 in which the compound is H.Tyr(3-$^{125}$I).D-Ala.Gly.Phe.D-leu.OH and salts thereof.

9. An assay method according to claim 1 wherein the radioiodinated compound is of the formula H—X$^1$—D—Ala—Gly—X$^4$—X$^5$—(X$^6$)$_n$—OH wherein
X$^1$ is L-tyrosyl substituted in the phenol moiety at the 2-position or at both the 2- and 6-positions (with respect to the hydroxy group) with an iodine radioisotope;
D-Ala is D-alanyl;
Gly is glycyl;
X$^4$ is selected from L-phenylalanyl and L-4-chlorophenylalanyl;
X$^5$ is selected from L-leucyl, D-leucyl, L-methionyl, D-methionyl, L-norleucyl and D-norleucyl;
X$^6$ is L-threonyl;
and n is selected from 0 and 1;
together with their salts and esters, wherein the group X$^1$ has a single iodine radioisotope substituent in the phenol moiety thereof, said substituent located at the 2-position (with respect to the hydroxy group) and selected from $^{125}$I and $^{131}$I.

10. An assay method according to claim 9 wherein the iodine radioisotope is $^{125}$I.

11. An assay method according to claim 1 wherein the opiate receptor material is or is derived from cells of a cell line possessing opiate receptors.

12. An assay method according to claim 11 wherein the cell line is the neuroblestoma X glioma hybrid NG108-15.

13. An assay method according to claim 1 wherein the opiate receptor material is derived from mammalian brain tissue.

14. An assay method according to claim 13 wherein the opiate receptor material is derived from calf or ox brain.

15. An assay method according to claim 13 wherein the opiate receptor material is a synaptic membrane-containing fraction of brain tissue.

* * * * *